United States Patent [19]

Fujita

[11] 4,378,147
[45] Mar. 29, 1983

[54] ADAPTOR FOR USE WITH OPHTHALMOLOGICAL MICROSCOPE

[75] Inventor: Susumu Fujita, Kobe, Japan

[73] Assignee: Konan Camera Research Institute, Nishinomiya, Japan

[21] Appl. No.: 184,328

[22] Filed: Sep. 5, 1980

[30] Foreign Application Priority Data

Sep. 13, 1979 [JP] Japan ............................. 54-118433
Dec. 28, 1979 [JP] Japan ............................. 54-171587

[51] Int. Cl.³ ........................... A61B 3/10; A61B 3/14
[52] U.S. Cl. ................................... 351/205; 351/206; 351/219
[58] Field of Search ............... 351/6, 7; 350/418, 447; 354/62

[56] References Cited

U.S. PATENT DOCUMENTS

| | | | |
|---|---|---|---|
| 1,954,755 | 4/1934 | Heine | 350/447 X |
| 3,409,349 | 11/1968 | Boyle et al. | 351/6 |
| 4,061,423 | 12/1977 | Pomerantzeff | 351/16 |
| 4,067,646 | 1/1978 | Nohda | 351/16 X |

Primary Examiner—John K. Corbin
Assistant Examiner—Rodney B. Bovernick
Attorney, Agent, or Firm—Wenderoth, Lind & Ponack

[57] ABSTRACT

An adaptor for use with an objective lens in an ophthalmological microscope comprises of an eyepiece member having an aperture defined therein for containing an impregnating liquid having a refractive index intermediate those of the objective lens and the cornea to be observed and a collar member for supporting said eyepiece member in fixed relation to the objective lens. The improvements wherein said collar member has a passage through which said impregnating liquid is adapted to be introduced into said aperture.

8 Claims, 7 Drawing Figures

ADAPTOR FOR USE WITH OPHTHALMOLOGICAL MICROSCOPE

The present invention relates to an ophthalmological microscope, or ophthalmoscope, for observing an interior of an eyeball, and more particularly to an adaptor for use with the objective lens of the ophthalmological microscope for supporting an impregnating liquid between the front surface of the objective lens and the surface of the eyeball to be observed.

Figure 1:
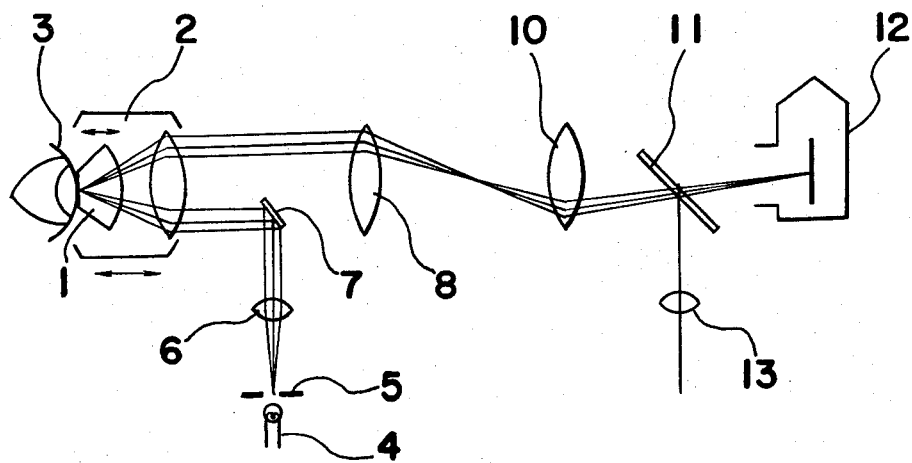

There has been proposed an ophthalmological microscope, or ophthalmoscope in the art and an example thereof is disclosed in Japanese Laid-Open Patent Application No. 99647/1979, laid open to public inspection on Aug. 6, 1979, and shown in FIG. 1.

As shown schematically in FIG. 1, the objective lens assembly 2 of the microscope of this type includes, as one of its lens elements, a cone lens 1 usually made of glass, which serves to increase the angle of view so that an ophthalmologist looking the eyeball through the microscope can observe a relatively large area of the endothelia of the eyeball.

In use of the microscope, the front face of the cone lens is put into contact with the surface of the eyeball 3, and an illuminating light, which is obtained through an illuminating optical system including an illuminating lamp 4, a slit 5, a condenser lens 6 and a reflective mirror 7, is introduced from one side of the optical axis of the microscope and projected onto the eyeball 3 through the cone lens 1. In this arrangement, the light reflected from the surface of the cornea and/or the endothelia is transmitted through the objective 2 to the focusing lens assembly 8, and the image so focused by the focusing lens assembly 8 is, after having been enlarged by the lens 10, splitted into two directions by the beam splitting half-mirror 11. The image carrier light component so splitted into one direction by the half-mirror is introduced into the camera 12 and photographed subsequently on the photographic film. The other image carrier light component deflected by the half-mirror in the other direction is observed through the eyepiece 13.

In such a microscope as mentioned above, however, the intensity of the light reflected by the surface of cornea is too high, for instant, approximately ten times the intensity of light reflected by the endothelia, to observe the endothelia clearly. This means that the presence of the high intensity of the reflected light, owing to the interference with the light reflected by the endothelia, reduces the field of view of the endothelia in the eyeball. This is caused by the fact that there is a large difference between the refractive index of the cone lens and the refractive index of the cornea to which the cone lens contacts directly or through a very thin layer of impregnating liquid.

To solve this problem, an adaptor for use with the objective of the microscope has been proposed in a U.S. patent application No. 139,142 filed on Apr. 10, 1980, a GB patent application No. 8012066 filed on Apr. 11, 1980 or a German Patent Application, all corresponding to a combination of both the Japanese Patent Application Nos. P 56560/79 and P 143625/79, and the Japanese Utility Model Applications U 61440/79, U 153887/79, U 153888/79 and U 177512/79.

As disclosed in these prior applications, the adaptor is of one piece construction including an eyepiece member and a collar, the eyepiece member having an aperture defined therein for containing an impregnating liquid such as a physiological saline solution having a refractive index which is intermediate those of the cone lens and the cornea. The collar protrudes from the eyepiece member in one direction in alignment and coaxial relation with the aperture in the eyepiece member and is so formed as to fit around the outer peripheral portion of the cone lens of the microscope and to support the eyepiece member in fixed relation to the cone lens.

When the adaptor is used, it is possible to reduce the amount of the light which would be reflected by the surface of the cornea since the adaptor is effective to retain an impregnating liquid layer of a constant thickness in the form as intervened between the surface of the eyeball and that of the cone lens of the microscope, so that the interior of an eyeball can be observed very clearly without being disturbed by the light reflected by the eyeball surface.

As mentioned above, the proposed adaptor has great advantages. However, it still has some disadvantages to be solved or to be improved, for example, a difficulty to fill impregnating liquid into the aperture of the eyepiece member without any formation of air bubbles, which would be formed because of the smallness of the aperture and, also, a difficulty to remove bubbles once formed during the observation being made. Such bubbles makes the observation impossible, and, if not impossible at all, hard to be performed.

Accordingly, it is one object of the invention to provide an adaptor for use with an objective lens in an ophthalmological microscope which is effective to retain an impregnating liquid between the objective lens and the eyeball without any formation of air bubbles.

It is another object of the invention to provide an adaptor effective to expel air bubbles by additionally filling an impregnating liquid when such air bubbles have been formed during the observation being made.

In accordance with the invention, an adaptor comprises a collar member having a passage through which an impregnating liquid is adapted to be introduced into the aperture of the eyepiece member constituting a part of the adaptor together with said collar member. This passage desirably may be a slit-like passage which extends longitudinally of said collar member from one point on the outer surface thereof to said aperture and terminates in communication with.

In use of the adaptor according to the invention, an operator or opthalmological inspector only drops an impregnating liquid, by the use of, for instance, a proper squirt onto said one point of the passage, allowing the impregnating liquid to flow through the passage onto said aperture of said eyepiece. By so doing, the impregnating liquid fills the aperture in the eyepiece member while discharging air in the aperture to the outside of the eyepiece member.

Figure 2:
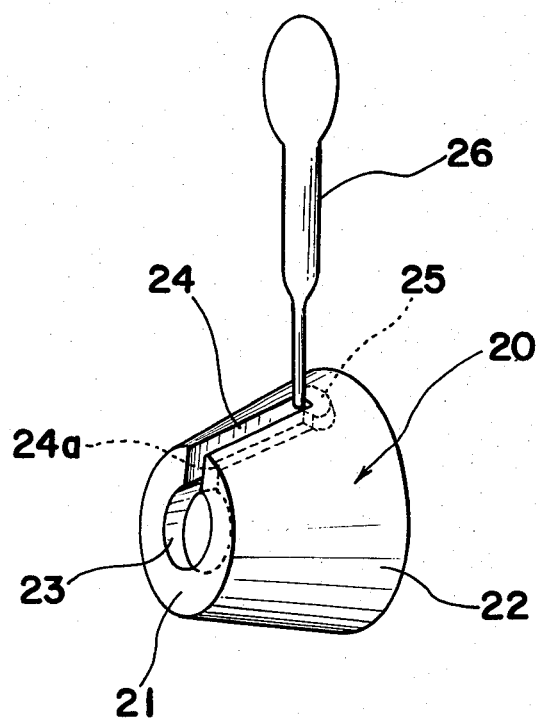
Figure 3:
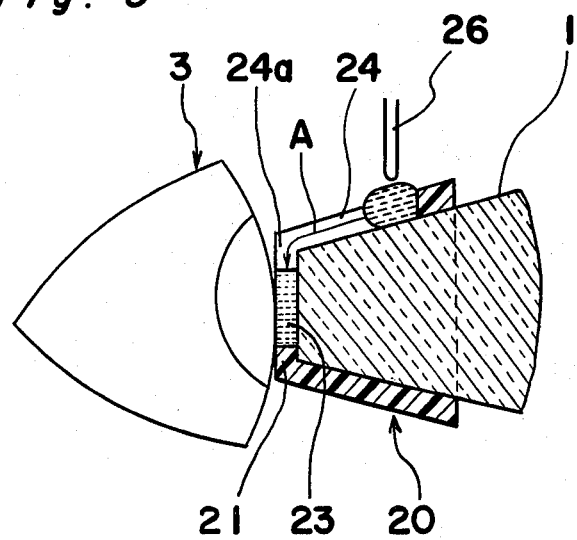
Figure 4:
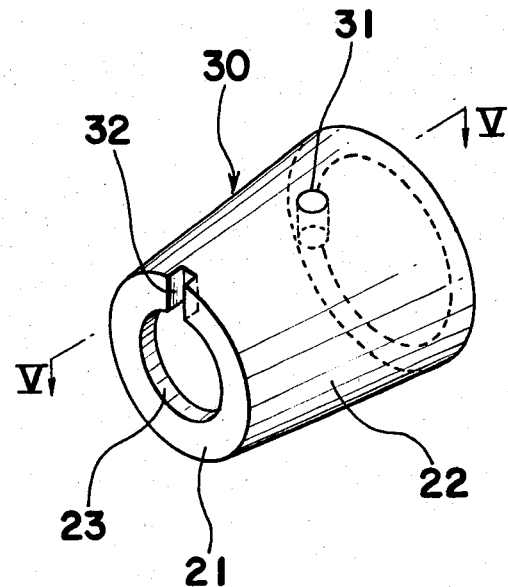
Figure 5:
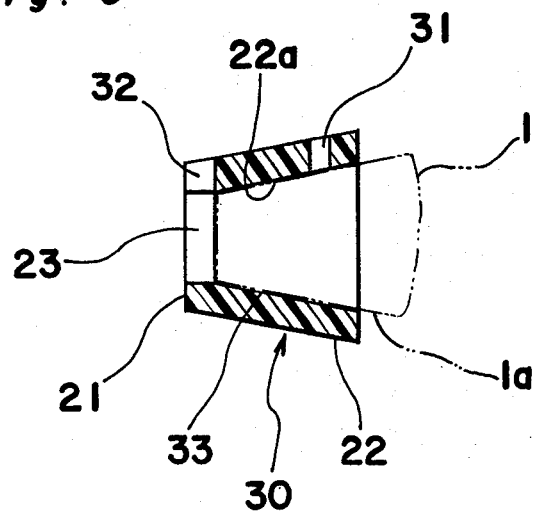
Figure 6:
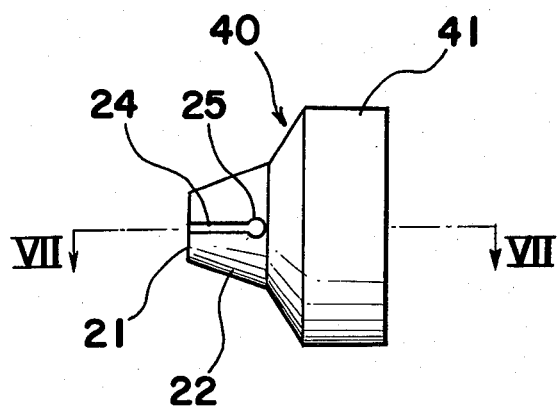
Figure 7:
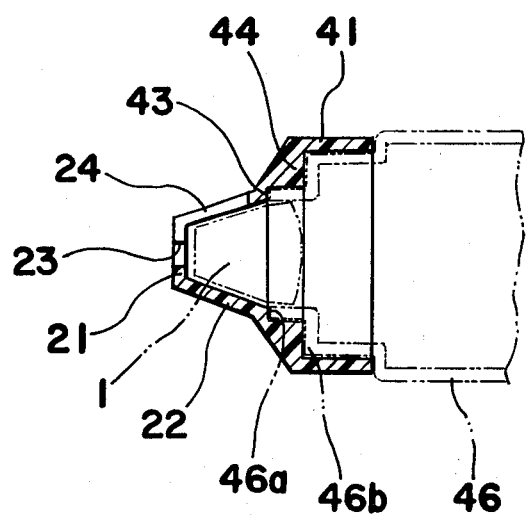

Other features and advantages of the present invention will become apparent from the following description when taken in conjunction with the accompanying drawings, in which;

FIG. 1 is a schematic diagram representing an optical system of the conventional ophthalmological microscope to which the present invention is applicable, FIG. 2 is a perspective view of an adaptor according to one embodiment of the present invention, FIG. 3 is a longitudinal sectional view of the adaptor shown in FIG. 2, said adaptor being shown as held in contact with an eyeball to be observed, FIG. 4 is a perspective view of an adaptor according to another embodiment of the present invention, FIG. 5 is a cross sectional view taken along the line V—V in FIG. 4, FIG. 6 is a plan view of an adaptor according to a further embodiment of the present invention, and FIG. 7 is a cross sectional view taken along the line VII—VII in FIG. 6.

As shown in FIGS. 2 and 3, an adaptor 20 made of plastics is of one piece construction including an eyepiece member 21 and a collar member 22. The eyepiece member is in the form of a circular disk of uniform thickness and of a diameter, for example 2~3 mm, required to fit to an eyeball 3 to be observed. The eyepiece member 21 has a circular aperture 23 defined therein for containing an impregnating liquid such as a physiological saline solution.

The collar member 22 protrudes from the outer periphery of the eyepiece member 21 in one direction in alignment and coaxial relation with the aperture 23 and is so formed as to receive therein the cone lens 1 of the ophthalmological microscope as described previously with reference to FIG. 1.

In accordance with the present invention, there is provided in the collar member 22 a slit-like passage 24 through which the impregnating liquid is adapted to be introduced into the aperture 23. The slit-like passage 24 extends longitudinally of the collar member 22 from one point on the outer surface thereof remote from the eyepiece member 21 to said aperture 23 and terminates in communication with said aperture 23.

As shown in FIG. 3, the slit-like passage 24 is defined in, and cut completely through the thickness of, the wall of the collar member 22. The width of the slit-like passage 24 is so selected as to enable the impregnating liquid to flow under a capillary action towards the aperture 23, and it may be, for instance, 0.5 mm.

It is desirable that one end of the passage 24 remote from the aperture 23 is enlarged, as shown by phantom line 25 in FIG. 2, so that a drop of the impregnating liquid applied by the use of a squirt 26 can be received therein.

In use of said adaptor 20, the adaptor 20 is first mounted by fitting to the cone lens 1 of the ophthalmological microscope. When the adaptor 20 is so mounted, the slit-like passage 24 is preferably positioned a top of the cone lens 1 to enable one or more drops of the impregnating liquid to be contained in one end of the passage 24 remote from the aperture 23. Thereafter, as indicated by the arrow A, the impregnating liquid so supplied from the squirt 26 is introduced smoothly and quickly through the slit-like passage 24 by the capillary action into the aperture 23 in the eyepiece member 21. The continuously introduced impregnating liquid gradually fills the aperture 23, while discharging air in the aperture 23 through a radially extending portion 24a of the slit-like passage 24.

The supply of the impregnating liquid can be done prior to the mounting the adaptor 20 to the cone lens 1 or after the mounting. It is also possible, as shown in FIG. 3, after eyepiece member 21 has been held in contact the eyeball 3. Moreover, it is possible to add the impregnating liquid in order to remove air bubbles formed during the observation.

In any case, a layer of the impregnating liquid of uniform thickness is intervened between the front face of the cone lens 1 and the surface of the eyeball without air bubbles formed therebetween. Owing to the intervention of the layer which has a refractive index intermediate those of the cone lens 1 and the cornea, it is possible to reduce the possible interference with the light which would be reflected from the surface of the cornea and to observe the endothelia clearly without being disturbed by said light reflected from the surface of the cornea.

In the adaptor 30 shown in FIG. 4 and FIG. 5, the collar member 22 has a hole 31 defined therein for the introducing of the impregnating liquid into a clearance 33 between the collar member 22 and the peripheral face of the cone lens 1, and the eyepiece member 21 has a radially extending slot 32 defined therein for the discharge of air in the aperture 23 in the eyepiece member 21.

The hole 31 is of a circular cross section perforated completely through the thickness of the wall of the collar member 22. The slot 32 is formed by notching inwardly from the front face so as to communicate the aperture 23 to the outer periphery of the eyepiece 21 in the radial direction thereof.

In the embodiment of FIGS. 4 and 5, the clearance between the inner surface 22a of the wall of the collar member 22 and the outer surface 1a of the cone lens 1 serves as a passage through which the impregnating liquid is introduced into the aperture 23. In other words, the impregnating liquid once dropped into the hole 31 is introduced into the aperture 23 of the eyepiece member 21 by the capillary action through said clearance 33.

The slot 32 of the eyepiece member 21 serves only to discharge air in the aperture 23 as the impregnating liquid is introduced in the aperture 23 in a gradually increasing amount.

In the adaptor 40 shown in FIGS. 6 and 7, the collar member 21 thereof is further provided with an annular flange 41 for mounting said adaptor on any known objective lens barrel 46 of the ophthalmological microscope, said objective lens barrel 46 being shown by the phantom line in FIG. 7.

The annular flange 41 has first and second annular shoulders 43 and 44 defined in the inner wall 45 of the annular flange 41 coaxially with the collar member 21.

The first annular shoulder 43 is defined adjacent the boundary between the collar member 21 and the annular flange 41 and serves to position the adaptor 40 correctly relative to the annular end face 46a of the barrel 46 in which the cone lens 1 is held. The second annular shoulder 44 having a larger radius than that of the first shoulder 43 serves to position the adaptor 40 correctly relative to the annular step portion 46b of the barrel 46 in which the objective lens assembly other than the cone lens is held.

Although the present invention has been described in connection with the preferred embodiments thereof with reference to the accompanying drawings, it should be noted that various changes and modifications are apparent to those skilled in the art. For example, the adaptor according to the present invention is also applicable to the type of ophthalmological microscope which has a objective lens other than the cone lens 1.

What is claimed is:

1. An adaptor for use with an objective lens in an ophthalmological microscope comprised of an eyepiece member having an aperture defined therein for containing an impregnating liquid having a refractive index intermediate those of the objective lens and the cornea to be observed and a collar member for supporting said eyepiece member in fixed relation to the objective lens, said collar member protruding from said eyepiece member in one direction in alignment and coaxial relation with said aperture in said eyepiece member and being so formed as to receive therein the objective lens of the ophthalmological microscope, the improvement wherein said collar member has a passage through which said impregnating liquid is adapted to be introduced into said aperture, said passage extending longitudinally of said collar member and having one end positioned on the collar member and remote from the aperture and the other end communicated to the aperture.

2. An adaptor according to claim 1, wherein said passage is in the form of a slit cut completely through the thickness of the wall of the collar member and wherein said eyepiece member having a passage for discharging air in said aperture in the radial direction thereof.

3. An adaptor according to claim 1, wherein said eyepiece member and said collar member are of one-piece construction.

4. An adaptor according to claim 2, wherein said passage for discharging air is communicated to said passage.

5. An adaptor according to claim 1, 2, 3 or 4, wherein said one end of the passage is enlarged in size for receiving at least one drop of impregnating liquid therein.

6. An adaptor according to claim 1, wherein the objective lens includes a cone lens for increasing the angle of view and said collar member is adapted to receive therein an outer peripheral portion of said one lens.

7. An adaptor according to claim 1 or 6, wherein said collar member has an annular flange for mounting said adaptor on an objective lens barrel of the ophthalmological microscope with the aperture aligned coaxially with the optical axis of the objective lens, said annular flange having a larger inner diameter than the inner diameter of said collar member.

8. An adaptor according to claim 7, wherein said annular flange has an interior wall formed with at least one annular shoulder defined adjacent the boundary between said collar and said flange, said shoulder serving to position said adaptor correctly relative to the objective lens assembly of the ophthalmological microscope.

* * * * *